United States Patent [19]

Weissman

[11] 4,260,383

[45] Apr. 7, 1981

[54] DENTAL RETAINING SPLINT

[75] Inventor: Bernard Weissman, New York, N.Y.

[73] Assignee: Ipco Hospital Supply Corporation, White Plains, N.Y.

[21] Appl. No.: 70,247

[22] Filed: Aug. 27, 1979

[51] Int. Cl.³ .............................................. A61C 5/04
[52] U.S. Cl. ...................................... 433/225; 433/76
[58] Field of Search .................. 433/225, 229, 215, 76

[56] References Cited

U.S. PATENT DOCUMENTS

| | | | |
|---|---|---|---|
| 3,822,472 | 7/1974 | Garfinkel | 433/215 |
| 4,177,565 | 12/1979 | Heasley | 433/75 |

Primary Examiner—Robert Peshock
Attorney, Agent, or Firm—Friedman, Goodman & Teitelbaum

[57] ABSTRACT

A dental retaining splint is disclosed including a bar-like body member having preferably two tubular members extending perpendicularly therefrom, where the tubular members have axial openings extending therethrough. The body member has an H-shaped configuration with the front and rear walls being serpentined to define sections therein. These sections can be removed, such as by cutting, to provide a shorter splint. In use, the splint is first temporarily held in a channel formed in adjacent teeth, where the tubular members function as guides for a drill to form pilot holes in the teeth. The splint is then removed, and the pilot holes function as lead holes for the formation of enlarged bores to receive the tubular members therein for retaining the adjacent teeth in a fixed position. The splint is then replaced so that the tubular members are disposed in the bores formed therefor. An inlay fills in the channel and covers the splint in the final procedure step. Accordingly, the splint structure can be formed wider, longer, and include additional tubular members to fulfill particular dental requirements.

26 Claims, 28 Drawing Figures

DENTAL RETAINING SPLINT

BACKGROUND OF THE INVENTION

The present invention relates to dentistry in general, and more particularly to a dental retaining splint for the reinforcement and retention of mobile dentition in the mouth, and to the method for securing the splint to the dentition.

The use of splint structure disposed along the lingual surfaces of anterior teeth for reinforcing natural teeth is well known in the art. However, the formation of such prior art splints and there application are accompanied by serious limitations, such as the requirement that the securing pins for the splint structure must be disposed in horizontal parallelism. As a consequence, it has been found to be impractical, if not impossible, to apply such prior art splints to other than the anterior teeth, where it is necessary to utilize involved and complicated procedures in the preparation of the teeth and to utilize special equipment in order to assure the required horizontal parallelism. This procedure, from the point of view of the dentist, has been involved and time consuming and also is a source of considerable discomfort to the patient.

A procedure for overcoming the above-mentioned prior art problems is disclosed in my U.S. Pat. No. 3,348,311. However, this patented procedure involves forming apertures in the teeth, forming an impression of the involved dental area, forming a cast model from the impression including the apertures, inserting a threaded pin through the apertures in cast model, putting a threaded nut on the pin, then forming a wax-up of the desired splint and casting out a metal splint body by the lost wax process whereby the nuts are encased in the metal splint body, and finally disposing the splint body against the facial surfaces of the involved teeth and securing the splint body in place by means of a screw-threaded body into the nut encased in the splint. It is noted, that this patented procedure is not readily applied to the occlusal surfaces of the posterior teeth.

A dental retaining splint to further overcome the aforementioned prior art problems is disclosed in my U.S. Pat. No. 3,487,545. This patented splint includes a band of dental metal provided with a plurality of spaced, centrally located elongated apertures along its longitudinal dimension; and securing means having a head portion and a self-threading shank portion, where each shank portion is inserted through one aperture and is self-threaded into the tooth to secure the splint band thereto, with the head portion retaining the splint band in position on the tooth being reinforced thereby. This patented splint does not provide a high degree of resistance to vertical and horizontal loading which is required in dental splinting applications. Furthermore, the positioning of the self-threading securing means does not provide for specific locations to avoid the hazzards relative to root perforation of pulpal involvement. Furthermore, for proper securement, more than one securing means may be required to be self-threaded into one tooth.

SUMMARY OF THE INVENTION

Accordingly, it is an object of the present invention to provide a dental retaining splint for the reinforcement and retention of mobile dentition in the mouth which overcomes the disadvantages of the prior art.

Another object of the invention is to provide a dental retaining splint which may be readily secured to the dentition desired to be reinforced and retained with a minimum amount of the preparation and discomfort to the patient.

A further object of the present invention is to provide a dental retaining splint which may be fabricated in a simple, efficient and economical manner with the required accuracy for accomplishing the desired ends.

Still another object of the present invention is to provide a procedure for the installation of the dental retaining splint in the mouth with a minimum amount of discomfort to the patient.

Yet another object of the present invention is to provide a dental retaining splint having a bar-like body member and preferably two tubular members extending perpendicularly therefrom, where the tubular members are retained in bores formed in the teeth desired to be reinforced and retained.

An added object of the present invention is to provide a dental retaining splint as set forth above, where openings in the tubular members function as guides for a drill to form pilot holes used in the formation of the bores which receive the tubular members.

An yet an added object of the present invention is to provide a dental retaining splint of the type described above which has an H-shaped body member with serpentined front and rear walls to define sections therein, where these sections can be removed to provide a shorter splint.

A still further object of the present invention is to provide a dental retaining splint of the type described above which is adapted to function with a wider body portion and/or a longer body portion and/or additional tubular members and/or with only one tubular member.

These objects are achieved in accordance with a preferred embodiment of the present invention, where the dental retaining splint comprises a bar-like body member having tubular means extending perpendicularly therefrom, where the tubular means have axial openings therethrough. The body member is fabricated with an H-shaped configuration, wherein the front and rear walls thereof are serpentined to define sections therein which can be removed, such as by cutting, to provide a shorter splint. In the dental procedure, the splint is first temporarily held in a channel provided in adjacent teeth in a conventional manner, where the tubular means function as guides for a drill to form pilot holes in the teeth. After the pilot holes are formed, the splint is removed so that the pilot holes function as lead holes for the formation of enlarged bores to receive the tubular means therein for retaining adjacent teeth in a fixed position relative to each other. The splint is then replaced in the channel so that the tubular means are disposed in the bores, and then an inlay fills in the channel to cover the splint. Accordingly, in other embodiments of the present invention, the splint structure is formed wider for added strength thereof, is made longer to reinforce and retain larger and/or additional teeth, and may include additional tubular means for the reinforcement and retention of a plurality of teeth to fulfill particular dental requirements.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 17 being a top plan view, FIG. 18 being a front elevational view and FIG. 19 being a side elevational view thereof;

FIG. 20 being a top plan view, FIG. 21 being a front elevational view and FIG. 22 being a side elevational view thereof;

FIG. 23 being a top plan view and FIG. 24 being a front elevational view;

FIG. 27 being a top plan view and FIG. 28 being a front elevational view thereof.

In the various Figures of the drawings like reference characters designate like parts.

DETAILED DESCRIPTION OF THE PREFERRED EMBODIMENT

Figure 1:
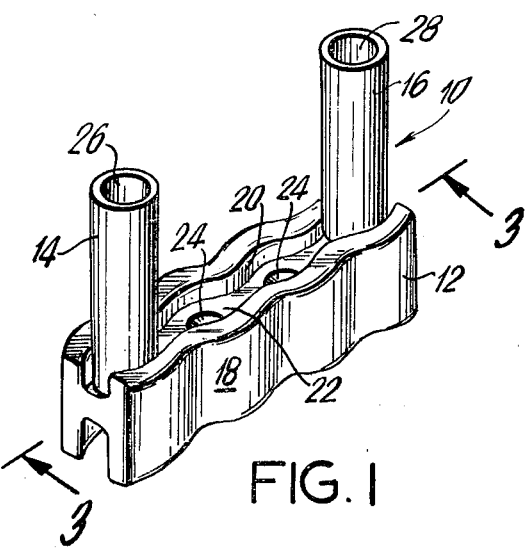
FIG. 1 is a perspective view illustrating the dental retaining splint pursuant to the present invention.
Figure 2:
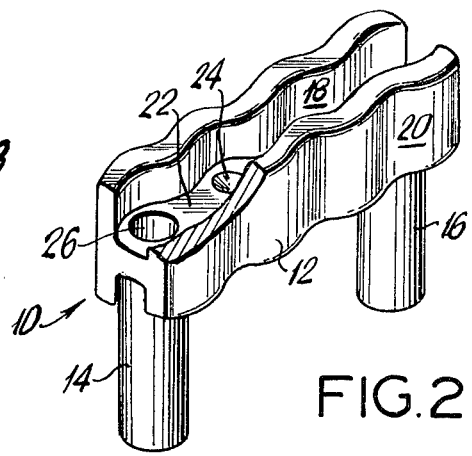
FIG. 2 is another perspective view, partly fragmented, illustrating the dental retaining splint facing in an opposite direction of that shown in FIG. 1.
Figure 3:
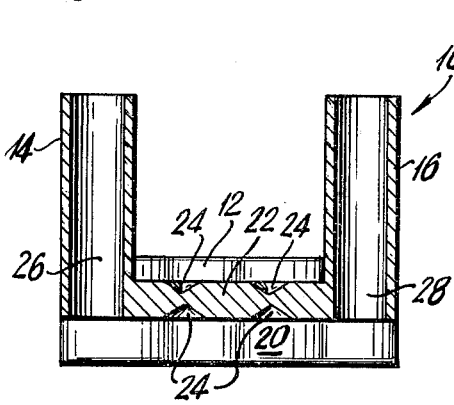
FIG. 3 is a cross-sectional view taken along line 3—3 of FIG. 1.

Referring now to the drawings, FIG. 1, 2 and 3 show a dental retaining splint 10 according to the present invention. The splint 10 comprises a bar-like body member 12 having two tubular members 14, 16 extending perpendicularly outwardly from opposite ends of the body member 12. The dental retaining splint 10 is fabricated from a metal material suitable for use in dentistry so that the splint can be disposed in a patient's teeth.

As indicated by an end view of the splint 10, the body member 12 has an H-shape to provide front and rear walls 18, 20 connected together by a longitudinally extending transverse wall 22 disposed therebetween. The tubular members 14, 16 extend outwardly from the transverse wall 22 with two sets of dimples 24 being provided in the upper surface and lower surface of the intermediate wall 22, the dimples 24 being disposed between the tubular members 14, 16. As shown in FIG. 3, the upper dimple 24 and lower dimple 24 of each set are in alignment with each other to reduce the thickness of the intermediate wall 22.

Figure 22:
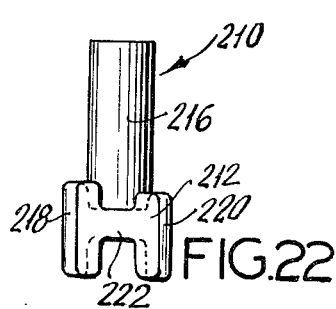

The front and rear walls 18, 20 are corrugated or serpentined with respect to each other to provide arcuate flanges about each tubular member 14, 16 which function as an added support to reinforce each tubular member, and also about each set of dimples 24, as best shown in FIGS. 1 and 2. Preferably, the rear wall 20 is slightly shorter in the direction of the tubular members than the front wall 18 in order to distinguish the front wall from the rear wall, where this difference in height is best shown in FIG. 22 which illustrates an elevational end view of the splint. This different in height also facilitates the removal of the splint from the teeth, as will be described more fully below.

Each of the tubular members 14, 16 include an axial opening 26, 28, respectively, extending completely therethrough. The function of the openings 26, 28 will be set forth in more detail below. It is noted, that the tubular members have an outer diameter of approximately 0.032 inches with the openings or inner diameter being approximately 0.024 inches. The tubular members extend approximately 0.072 inches above the body member, where the body member is approximately 0.152 inches in length with a height of approximately 0.045 inches and a width of approximately 0.056 inches. However, it is understood, that these above dimensions are given by way of example only, and can be changed according to the particular requirements of the splint.

Figure 4:
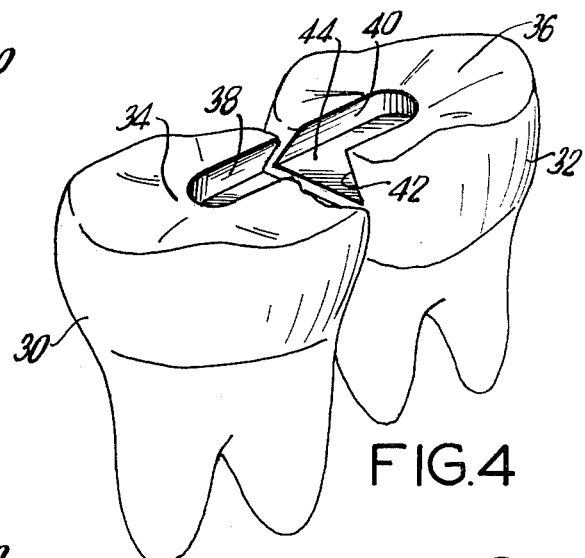
FIG. 4 is a perspective view illustrating two adjacent teeth provided with a channel to receive the dental retaining splint of the present invention.

Referring now to FIGS. 4–12, the operation of the present invention device will be described below. FIG. 4 shows 30, 32 of adjacent teeth, such as for example, the adjacent bicuspids, although it being understood that the present invention is equally applicable to and between other adjacent teeth, such as the cuspids, the molars, etc. In each occlusal surface 34, 36 of the crowns, a connecting channel 38 is formed therebetween in a conventional manner. Preferably, the walls 40, 42 of the channel are tapered to provide a wide base 44 at the bottom of the channel, where the tapered wall act to retain the inlay of dental material within the channel, as will be set forth hereinafter below. It is understood that the channel 38 is oversized to be larger than the body member 12 in length, width and height.

Figure 5:
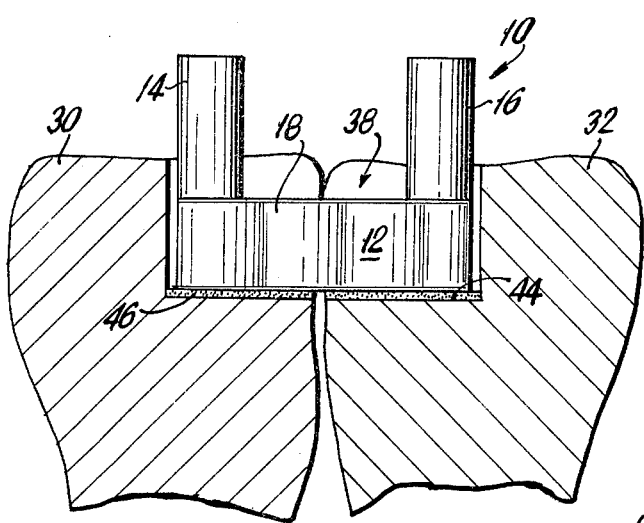
FIG. 5 is an elevational view, partly in cross-section, illustrating the initial positioning of the dental retaining splint in the channel provided therefor.

After the channel 38 is formed, a layer of temporary adhesive 46, such as wax or other suitable material, is disposed on the bottom surface of base 44 of the channel. The splint 10 is now positioned in the channel 38 with the tubular members 14, 16 extending outwardly therefrom, being temporarily held therein by the temporary adhesive 46, as shown in FIG. 5.

It is noted that frequently the base 44 of the channel 38 is uneven so that there may be a tendency for a flat surface disposed thereon to rock. However, the open portion between the walls 18, 20 of the body member 12 decreases the surface area of contact and in effect acts as two legs which are more stable than a flat bar. Furthermore, the spacing between the tubular members 14, 16, as indicated above, is such that the dental splint 10 can be positioned in the channel 38 to allow the drilling of holes to receive the tubular members, as will be discussed below so that there will be minimal hazards relative to root perforation or pulpal involvement.

Figure 6:
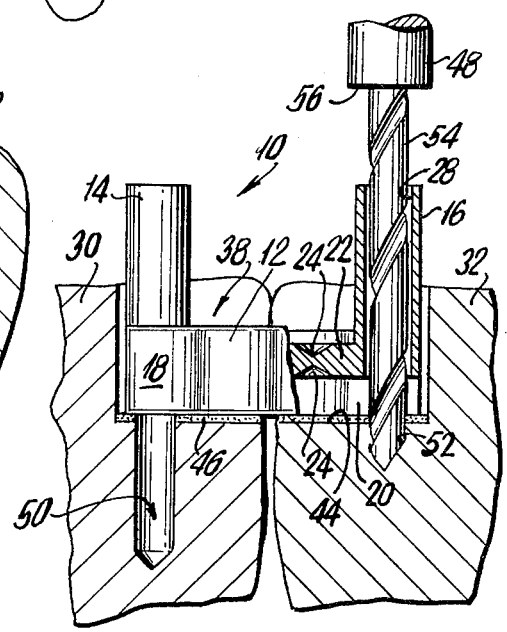
FIG. 6 is an elevational view illustrating the forming of the pilot holes in the teeth using the tubular members of the dental retaining splint as drilling guides.

Once the dental splint is secured in the channel 38, a pilot drill 48 is inserted into the openings 26, 28 of the tubular members 14, 16 and pilot holes 50, 52 are formed in the respective teeth, as shown in FIG. 6. Preferably, the drill bit 54 of the pilot drill 48 has a diameter approximately equal to or slightly less than the diameter of the openings 26, 28 of the tubular members so that the tubular members function as guides for the drill bit 54. Furthermore, the drill bit 54 has a pre-determined length in order to obtain the desired length of the pilot holes 50, 52. Accordingly, the pilot drill 48 is provided with a stop or an abutment 56 which will contact the upper portion of the tubular members when the desired length of the pilot holes 50, 52 has been reached.

Figure 7:
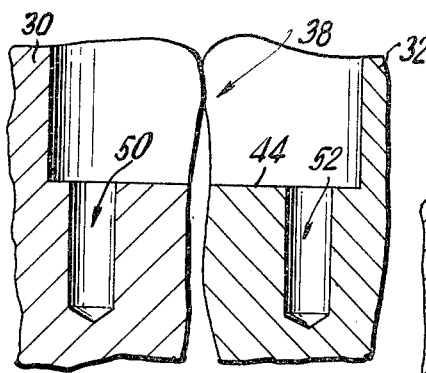
FIG. 7 is an elevational view illustrating the pilot holes extending from the channel provided in the teeth after the dental retaining splint has been removed.
Figures 8, 9:
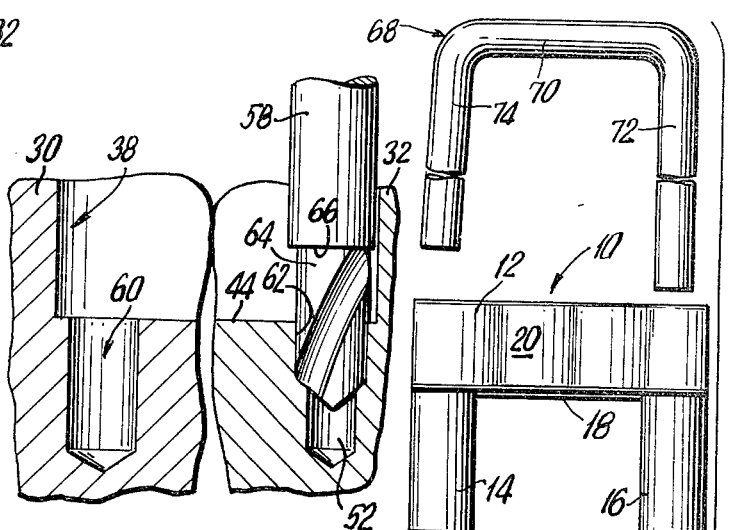
FIG. 8 is an elevational view illustrating the pilot holes functioning as lead holes for the forming of enlarged bores in the teeth.
FIG. 9 is an elevational view showing the dental retaining splint in combination with a positioning clip therefor.

After the pilot holes 50, 52 have been made, the splint 10 is removed from the channel 38, as shown in FIG. 7. Another dental drill 58 is now used to form bores 60, 62 in the teeth, where the pilot holes 50, 52 function as lead holes for drill bit 64 of the drill 58 in the formation of the bores as shown in FIG. 8. Here again, the drill bit 64 has a pre-determined length in order that the bores 60, 62 have desired selected lengths. Accordingly, the drill 58 is provided with a stop or abutment 66 which contacts the base 44 of the channel 38 when the desired length of the bores has been reached.

It should be noted at this point, that the space between the walls 18, 20 of the body member 12, in the position shown in FIG. 6 during the drilling of the pilot hole, has the added advantage in that it permits the escape of dentinal material carried to the surface by the drill bit 54 of the pilot drill 48, and also minimizes binding and other relted problems associated with deep-hole drilling procedures.

Due to the smallness of the splint 10, a positioning clip 68 has been provided therefor, as shown in FIG. 9. The clip has a bight 70 and two legs 72, 74, extending from opposite sides of the bight to define a U-shaped configuration. Preferably, the leg 72 is perpendicular to the bight 70 and the leg 74 is disposed at an angle to the bight 70, where this angle can be obtuse as shown or acute if desired. Furthermore, the leg 72 is preferably longer than the leg 74, where these legs 72, 74 can be made in any desired lengths. The distance from the remote free end of leg 72 to the remote free end of leg 74 is slightly greater than the distance between the axes of the tubular numbers 14, 16.

Figure 10:
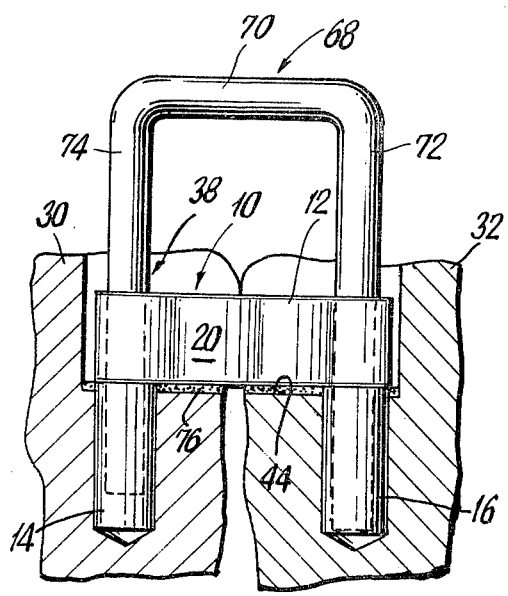
FIG. 10 is an elevational view illustrating the positioning clip being used to position the dental retaining splint in the prepared bores in the channel formed in the teeth.

In operation, the free end portion of the longer leg 72 is positioned in one of the openings of the tubular members, and then the end portion of the other leg 74 is tensioned inwardly and positioned in the opening of the other tubular member, after which time by means of the bight 70, the legs 72, 74 are pushed fully into the openings 26, 28 of the tubular members as indicated in FIG. 10. Therefore, the resiliency between the legs 72, 74 functions to hold the splint 10 thereon. Preferably, the diameters of the legs 72, 74 are approximately equal to or slightly less than the diameter of the openings 26, 28 of the tubular members. It should be noted, that the legs 72, 74 are inserted from the body member side of the splint 10 so that the free ends of the clip 68 are finally disposed near the free ends of the tubular members.

A layer of permanent adhesive 76, which is well known in the dentistry art, is disposed on the bottom surface or base 44 of the channel 38. By means of the clip 68, the splint 10 is now positioned in the channel 38 with tubular members 14, 16 disposed in the bores 60, 62 provided in the tooth therefor. It should be noted, that the drill bit 64 of the drill 58 has a diameter approximately equal to or slightly larger than the outside diameters of the tubular members 14, 16 so that the bores 60, 62 are large enough to receive the tubular members therein as best shown in FIG. 10.

Figure 11:
FIG. 11 is an elevational view illustrating the dental retaining splint permanently secured in the channel of the teeth, with the channel being filled with suitable dental material.

Once the dental splint 10 is secured in the channel 38, the positioning clip 68 is removed therefrom. An inlay 78 of dental restorative material, such as precious metal, amalgam, composite resin, ceramic, porcelain or other suitable material, is disposed in the channel 38 over the dental splint 10 as shown in FIG. 11, to cover and complete the dental procedure, where dental inlays are well known in the dentistry art. Thus, the tubular members 14, 16 function to retain the splint 10 in position to secure one tooth to its adjacent tooth, and the tapered walls 40, 42 of the channel retains the inlay 78 in the channel to hold the splint 10 therein.

It is noted that the U-shaped body member 12 of the splint provides excellent resistance to vertical and horizontal loading which is required in dental splinting applications. Furthermore, the inlay 78 fills the spaces between the walls 18, 20 which increases the strength characteristics of the body member 12. Additionally, the shorter rear wall 20 decreases the surface area of contact in the splint's final position where the longer front wall 18 is more in direct contact with the base 44 so that the tubular member 14, 16 can be properly fitted into the bores 60, 62. The shorter rear wall 20 also permits a dental tool to be inserted thereunder if it is desired to remove the splint from its final position.

Figure 12:
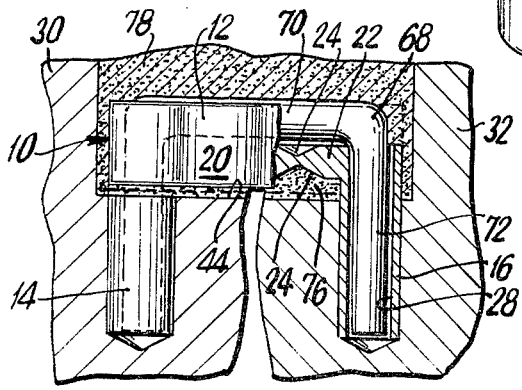
FIG. 12 is an elevational view similar to FIG. 11 showing the positioning clip disposed in the dental retaining splint to function as a reinforcing member.

FIG. 12 shows a modified form, where the positioning clip 68 is used to further strengthen the dental splint 10 and also to prevent any of the inlay 78 from entering into the openings of 26, 28 of the tubular members 14, 16. Accordingly, legs 72, 74 of the clip 68 are both cut shorter to approximately the same length as the tubular numbers 14, 16. Thus, the bight 70 of the clip 68 is pushed downwardly towards the body member 12 and rests against the transverse wall 22. Accordingly, inlay 78 is disposed over the splint 10 and the clip 68 positioned therein as shown in FIG. 12. It is noted that legs 72, 74 can be shortened by using any suitable dental cutting tool, where the cutting can be done with the clip 68 positioned in the splint 10 before the splint is inserted into channel 38 and bores 60, 62.

Figure 13:
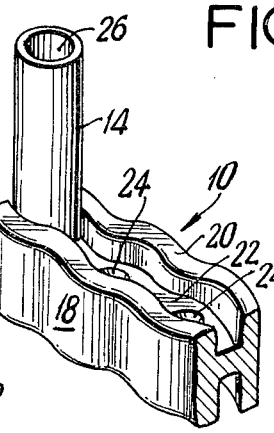
FIG. 13 is a perspective view illustrating the dental retaining splint having one tubular member cut off pursuant to the present invention.

In some situations, the length of the splint 10 may be too long depending upon the tooth size, the restoration required, the hazards relative to root perforation or pulpal involvement, and like instances. Accordingly, the present invention has made provisions for these types of situations. As shown in FIG. 13, in order to shorten the length of the splint 10, the tubular member 16 and base member portion associated therewith has been cut off, by using any suitable dental cutting tool well known in art. Accordingly, the serpentined walls 18, 20 function to divide the body member 12 into four sections defined by the indented portions therein between each section of arcuate flanges. Thus, as shown in FIG. 13, one section of arcuate flanges disposed around the tubular member 16 has been cut off so that the remaining three sections, including the tubular member 14, is the same as described above.

Figure 14:
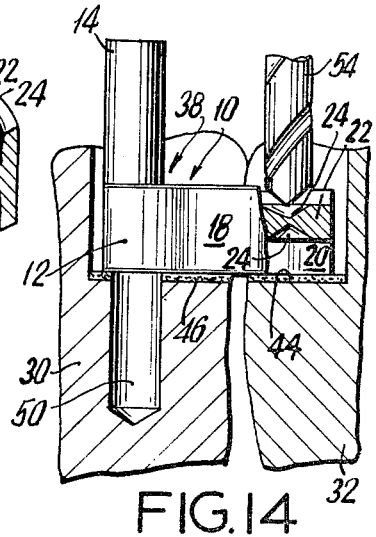
FIG. 14 is an elevational view illustrating the dental retaining splint of FIG. 13 being used to form the pilot holes in the teeth.
Figure 15:
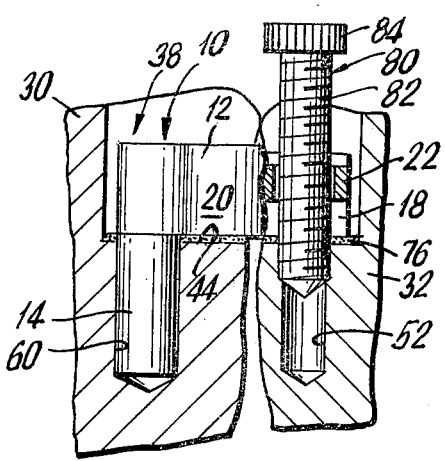
FIG. 15 is an elevational view illustrating a dental anchor being used to secure the dental retaining splint of FIG. 13 in one of the teeth.
Figure 16:
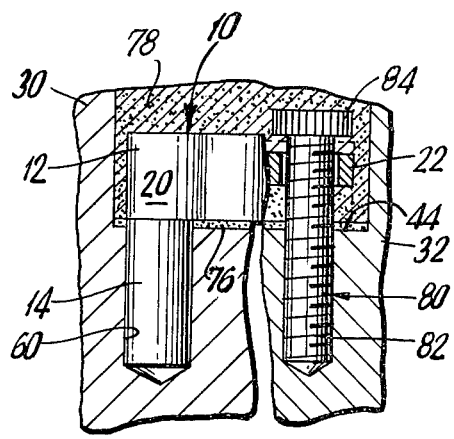
FIG. 16 is an elevational view illustrating the dental retaining splint of FIG. 13 permenently secured in the channel of the teeth, with the channel being filled with suitable dental material.

Referring now to FIGS. 14-16, operation of the shortened dental splint 10 will be described below. The first step is the formation of the channel 38 in the occlusal surfaces of the adjacent crowns 30, 32 in the same manner mentioned above. After the channel 38 is formed, the layer of temporary adhesive 46 is disposed on the base 44 of the channel. The shortened splint 10 is now positioned in the channel with the tubular member 14 extending outwardly therefrom, as shown in FIG. 14.

With the splint 10 being temporarily held in the channel, the pilot drill 48 is inserted into the opening 26 to form the pilot hole 50, in the same manner mentioned above. Now, the drill bit 54 of the pilot drill 48 is used to make a hole through the transverse wall 22, where the drill bit 54 is positioned in the dimple 24 which is at the thinnest portion of the transverse wall 22. The dimple 24 functions as a starting or pilot hole for the drill bit 54, being approximately the same size as the point of the drill bit. Furthermore, the arcuate flanges of the walls 18, 20 around the dimple 24 function as an indicator for the drill bit 54 in drilling a hole parallel to the first hole 50. Once the drill bit passes through the transverse wall 22, the drill bit 54 proceeds to form a pilot hole 52 in the crown 32. After both parallel pilot holes 50, 52 are formed, the shortened splint 10 is removed. It is noted, that the pilot hole 52 can be formed at an angle to the body member 12 other than perpendicular thereto when such an obtuse or acute angle is required.

When the splint 10 is removed, the dental drill 58 is used to form bore 60, using the pilot hole 50 as a lead hole in the same manner mentioned above. The dental drill 58, or any other suitable drill, is also used to enlarge the original hole through the transverse wall 22, for the reason set forth below.

The layer of permanent adhesive 76 is now disposed on the bottom surface or base 44 of the channel 38, and the shortened splint 10 is now positioned in the channel 38 with the tubular member 14 disposed in the bore 60 in the same manner set forth above. Once the dental splint 10 is secured in the channel 38, a dental anchor 80 having a self-threading shank portion 82 and an enlarged head 84, is inserted through the enlarged opening formed in the transverse wall 22. The dental anchor 80 is now self-threaded into the pilot hole 52 as shown in FIG. 15, where the enlarged hole in the transverse wall 22 prevents any binding between the splint and the dental anchor 80. Alternatively, instead of enlarging the original hole through the transverse wall 22, the pilot hole 52 can be enlarged as set forth above, and the dental anchor 80 can be self-threaded into the original splint hole for securement to the splint, where the shank portion is unthreadedly disposed in the enlarged hole in the tooth. It is noted, that if the pilot hole 52 is at an obtuse or acute angle as mentioned above, then the shank portion 82 will also be self-threaded at this desired angle, which may be required in some situations of restoration.

Once the dental anchor 80 is completely threaded into the pilot hole 52, with preferably the enlarged head 84 abutting against the body member 12, the inlay 78 is disposed in the channel 38 as shown in FIG. 16, in the same manner as set forth above.

It is noted that other types of dental anchors may be used in this procedure. Accordingly, if the dental anchor selected does not have an enlarged head thereon, the free end of the dental anchor may be bent onto the splint after the opposite end thereof has been self-threaded into the tooth. Accordingly, the dental anchor need not be self-threading and for that matter need not even be threaded, where the plug-in retention pin type of dental anchor may also be used with the device of the present invention.

Thus, as shown above, the dental splint 10 of the present invention can be cut and a section thereof removed to provide a smaller longitudinal length thereof. Accordingly, as set forth below, the dental splint can be further modified to fulfill specific dental requirements. It is understood, that the splint structures described below will be installed in the teeth in the same manner as set forth above, taking into account slight modifications thereof due to the structural differences therebetween. Furthermore, the rear wall adjacent to the tubular members is shorter than the front wall in each of the splints described below for the same reasons mentioned above.

Figure 17:
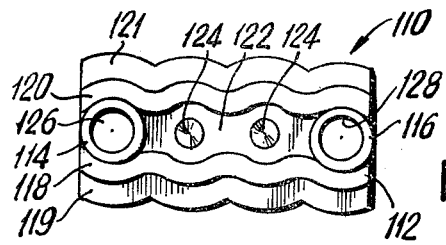
FIGS. 17, 18 and 19 illustrate a modification of the dental retaining splint pursuant to the present invention, this modified splint having a wider body portion.
Figure 18:
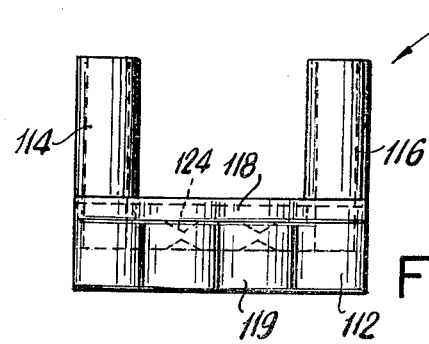
Figure 19:
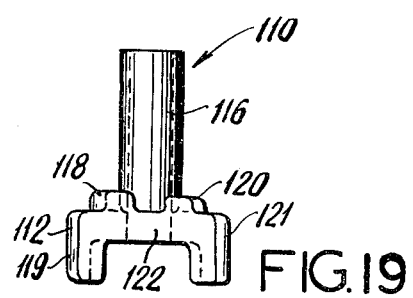

FIGS. 17, 18 and 19 show the top, front and end views of a modified dental retaining splint 110 according to the present invention. The main difference between splint 110 and the previously described splint 10 is that the modified splint 110 has a wider body portion to provide greater strength to resist heavy loading such as required in the molars. Accordingly, the splint 110 includes a bar-like body member 112 with tubular members 114, 116 extending perpendicularly from the body member. As shown in FIG. 19, the body member 112 is substantially H-shaped. The front and rear walls are serpentined to define four sections. The front wall portion 118 adjacent to the tubular members is closer to the rear wall portion 120 than the larger distance between the opposite front wall portion 119 and the opposite rear wall portion 121. The transverse wall 122 is disposed between the front and rear walls with the wall portions 118, 120 being on one side thereof and the wider spaced wall portions 119, 121 being on the other side thereof. Sets of dimples 124 are disposed in the transverse wall 122 between the tubular members, and the openings 126, 128 extend through the tubular members 114, 116, respectively.

Figure 20:
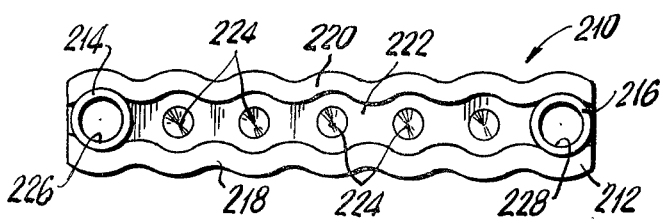
FIGS. 20, 21 and 22 illustrate a further modification of the dental retaining splint pursuant to the present invention, this modified splint having a longer body portion.
Figure 21:
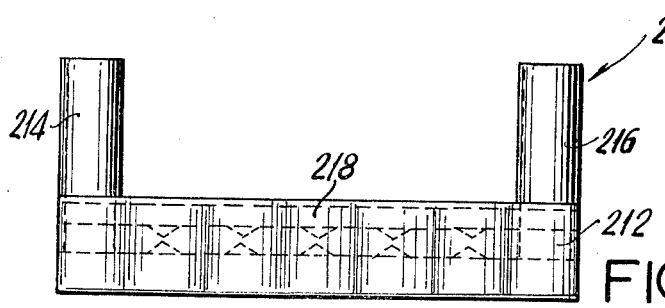

FIGS. 20, 21 and 22 disclose the top, front and end views respectively of a further modified dental splint 210 pursuant to the present invention, where this modified dental splint 210 has a longer body portion in the longitudinal direction than the above-mentioned dental splint 10. Here again, the splint 210 includes a bar-like body member 212 with two tubular members 214, 216 extending perpendicularly from the body member, the body member having a serpentined front wall 218, a serpentined rear wall 220 and a transverse wall 222 disposed therebetween to define an H-shaped configuration having seven sections therein. The transverse wall 222 is provided with five sets of dimples 224, where each set includes an upper and lower dimple, the dimples being disposed between the tubular members. Here again, the tubular members are provided with openings 226, 228 extending therethrough. It is noted that the end view shown in FIG. 22 is the same for the dental splint 10, and is also the same for the dental splint 410 disclosed in FIGS. 25 and 26 described below. Accordingly, because of its greater length, the splint 210 can be used for the larger molars, or can be used to retain three adjacent teeth with the tubular members 214, 216 being disposed in the first and third end teeth retained thereby.

Figure 23:
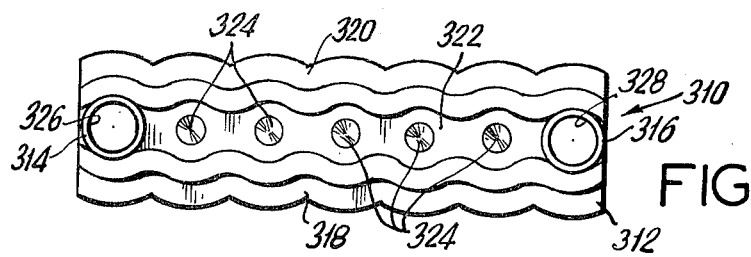
FIGS. 23 and 24 illustrate a modification of the dental retaining splint of FIGS. 20, 21 and 22 pursuant to the present invention, this modified splint having a wider body portion.
Figure 24:
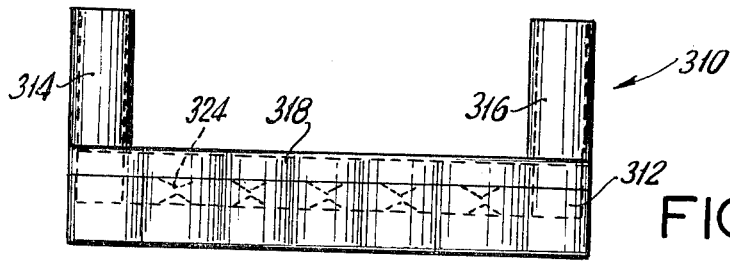

FIGS. 23, 24 disclose a modified dental splint similar to the above-mentioned dental splint 210, however, this modified dental splint 310 has a wider body portion to provide for the greater strength mentioned above. FIG. 23 is a top view and FIG. 24 is a front view. It is understood that the end view of splint 310 is the same as the end view of splint 110 shown in FIG. 19, and this end view is the same for the dental splint 510 shown in FIGS. 27 and 28 described below. Once again, the modified dental splint 310 includes a bar-like body member 312 having tubular members 314, 316 extending perpendicularly from the body member. The body member has serpentined front and rear walls 318, 320 and a transverse wall 322 disposed therebetween to define an H-shaped configuration having seven sections therein. It is noted, that the front and rear walls 318, 320 of splint 310 is similar to the front and rear walls of splint 110 having closely spaced and wider spaced wall portions, so that a further description thereof is not thought necessary. The transverse wall 322 is provided with five sets of dimples 324, where each set includes an upper and lower dimple, the dimples being disposed between the tubular members which are provided with the openings 326, 328 extending therethrough. It is noted, that this splint 310 can also be used for the larger molars or can be used to retain three adjacent teeth as set forth above with respect to dental splint 210.

Figure 25:
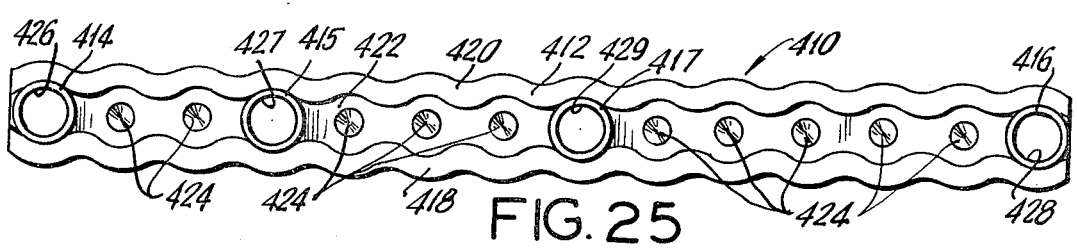
FIGS. 25 and 26 illustrate another modification of the dental retaining splint pursuant to the present invention, this modification dental splint having a longer body portion provided with additional tubular members, FIG. 25 being a top plan view and FIG. 26 being a front elevational view thereof.
Figure 26:
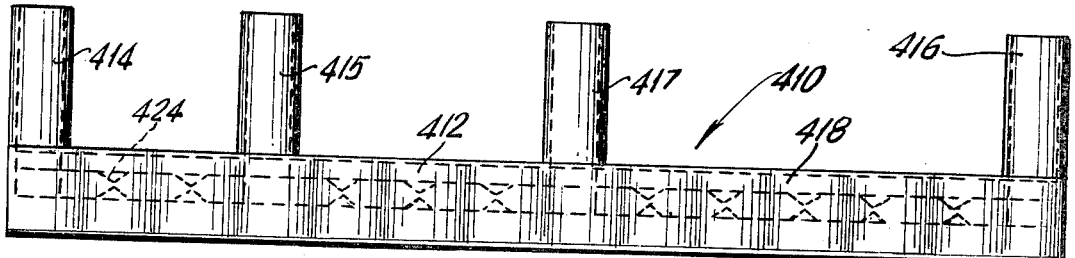

FIGS. 25 and 26 disclose the top and front views of a further modified dental splint 410 pursuant to the present invention, where this modified dental splint 410 has a still longer body member than the two above-mentioned dental splints 10 and 210. Furthermore, dental splint 410 is provided with two additional tubular members so that dental splint 410 can be secured to a plurality of teeth, as much as four or five teeth, where the body member 412 can be bent along its longitudinal length in order to be properly aligned within a channel formed in this group of teeth. Additionally, dental splint 410 lends itself to be separated into desired lengths to meet specific dental requirements where this splint can easily be cut into two or three lengths to be secured in different channels as required. Specifically, the splint 410 includes a bar-like body member 412 with four tubular members 414, 415, 416 and 417 extending perpendicularly from the body member, the body member 65 having a serpentined front wall 418 and a serpentined rear wall 420 and a transverse wall 422 disposed therebetween to define an H-shaped configuration having fourteen sections therein. The transverse wall 422 is provided with three groups of dimples 424 determined by the positions of the tubular members, one group having two sets of dimples, the second group having three sets of dimples and the third set having five sets of dimples, where each set includes an upper and lower dimple, and each group of dimples is disposed between associated tubular members. Once again, the tubular members are provided with openings 426, 427, 428 and 429 extending therethrough.

Figure 27:
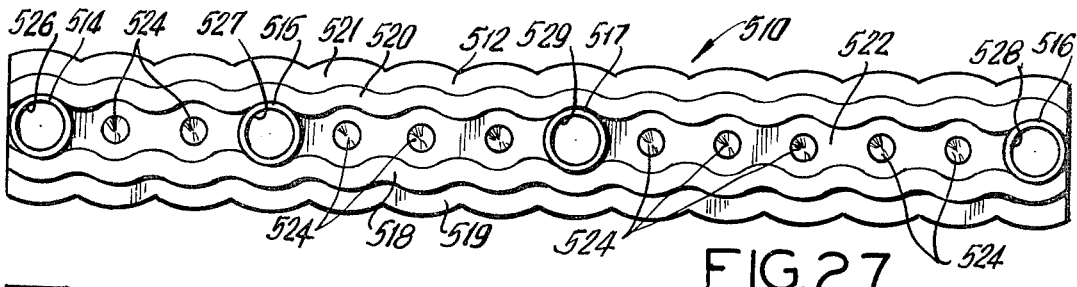
FIGS. 27 and 28 illustrate a modification of the dental retaining splint of FIGS. 25 and 26 pursuant to the present invention, this modified splint having a wider body portion.
Figure 28:
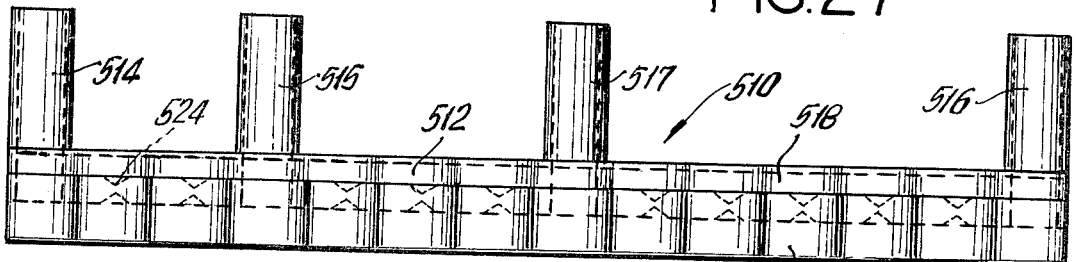

FIGS. 27 and 28 disclose a modified dental splint similar to the above-mentioned dental splint 410, however, this modified dental splint 510 has a wider body portion to provide for the greater strength mentioned above. The features of dental splint 510 is the same as those features mentioned above with respect to splint 410 and therefore it is not thought necessary to repeat these features. The modified dental splint 510 includes a bar-like body member 512 having four tubular members 514, 515, 516 and 517 extending perpendicularly from the body member. The body member 512 is substantially H-shaped with the front and rear walls being serpentined to define 14 sections therein. The front wall portion 518 adjacent to the tubular members is closer to the rear wall portion 520 than the larger distance between front wall portion 519 and the opposing rear wall portion 521. The transverse wall 522 is disposed between the front and rear walls and is provided with three groups of dimples 524 determined by the positions of the tubular members, where these groups of dimples include two sets of dimples, three sets of dimples, and five sets of dimples as set forth above. The tubular members are provided with openings 526, 527, 528 and 529 extending therethrough.

Numerous alterations of the structures herein disclosed will suggest themselves to those skilled in the art. However, it is to be understood that the present disclosure relates to preferred embodiments of the invention which is for purposes of illustration only and is not to be construed as a limitation of the invention.

What is claimed is:

1. A dental retaining splint comprising:
a bar-like body member disposable in a channel extending from a first tooth to at least one adjacent tooth;
first retaining means extending outwardly from said body member for being disposed in a bore provided in the first tooth through a bottom wall of the channel, said first retaining means securing said body member to the first tooth when said body member is in a final position in the channel;
said first retaining means including at least one tubular member extending perpendicularly from said body member for being received in the bore of the first tooth;
said tubular member including guide means for guiding a drill during formation of a pilot hole in the first tooth when said body member is initially positioned in the channel with said tubular member disposed over and extending outwardly from the bottom wall of the channel, the pilot hole functioning as a lead hole for formation of the bore in the first tooth;
said guide means including an axial opening extending through said tubular member and through said body member; and
said body member including second retaining means longitudinally spaced from said tubular member for securing said body member to the adjacent tooth when said body member is in said final position.

2. A dental retaining splint according to claim 1, wherein said body member has serpentined means to provide longitudinally adjacent severable sections therein.

3. A dental retaining splint according to claim 1, wherein said body member has a second tubular member extending perpendicularly therefrom in the same direction as said first-mentioned tubular member to define said second retaining means for securing said body member to the adjacent tooth, said second tubular member including axial opening means extending therethrough for guiding the drill during formation of a pilot hole in the adjacent tooth.

4. A dental retaining splint according to claim 3, wherein said body member has a front wall, a rear wall and a longitudinally extending transverse wall disposed between said front and rear walls said tubular members extending outwardly from one side of said transverse wall.

5. A dental retaining splint according to claim 3, wherein said body member is serpentined to define longitudinally adjacent sections therein, said first-mentioned tubular member being disposed in one of said sections and said second tubular member being disposed in another one of said sections.

6. A dental retaining splint according to claim 5, wherin at least a third one of said sections includes a set of aligned dimples in one side and in the other side of said transverse wall to provide a reduced thickness in said transverse wall, said third section being disposed between said one section and said another one section.

7. A dental retaining splint according to claim 6, wherein said serpentined body member provides a set of arcuate flanges about said set of dimples, whereby each of said sections are severable to shorten said body member.

8. A dental retaining split according to claim 6, wherein said body member includes four sections, said one section with said first-mentioned tubular member being disposed at one end of said body member, said another one section with said second tubular member being disposed at an opposite end of said body member, and each intermediate section including one set of said aligned dimples.

9. A dental retaining splint according to claim 6, wherein said body member includes seven sections, said one section with said first-mentioned tubular member being disposed at one end of said body member, said another one section with said second tubular member being disposed at an opposite end of said body member, and each intermediate section including one set of said aligned dimples.

10. A dental retaining split according to claim 6, wherein said body member includes fourteen sections, said first-mentioned tubular member being disposed in a first section at one end of said body member, said second tubular member being disposed in a fourteenth section at an opposite end of said body member, a third tubular member being disposed in a fourth section from said one end of said body member, a fourth tubular member being disposed in an eighth section from said one end of said body member, and one set of said aligned dimples being disposed in each remaining section of said body member.

11. A dental retaining split comprising a bar-like body member having at least one tubular member, said tubular member extending perpendicularly from said body member for being received in a bore provided in a first tooth with said body member being disposable in a channel extending from the first tooth to at least one adjacent tooth, said tubular member including axial opening means extending therethrough for guiding a drill during formation of a pilot hole in the first tooth, said body member including means longitudinally spaced from said tubular member for securing said body member to the adjacent tooth, whereby the pilot hole functions as a lead hole for the formation of said bore in the first tooth, said body member having a front wall, a rear wall and a longitudinally extending transverse wall disposed between said front and rear walls to define an H-shaped configuration, said tubular movement being disposed between said front and rear walls and extending outwardly from one side of said transverse wall.

12. A dental retaining splint according to claim 11, wherein said front wall adjacent to said tubular member is longer than said rear wall opposite thereto and ajacent to said tubular member.

13. A dental retaining splint according to claim 11, wherein end portions of said front and rear walls adjacent to said tubular member on said one side of said transverse wall are closer to each other than opposite end portions of said front and rear walls on the other side of said transverse wall.

14. A dental retaining splint according to claim 11, wherein said front and rear walls are serpentined to define longitudinally adjacent sections therein.

15. A dental retaining splint according to claim 14, wherein at least one of said sections includes a set of aligned dimples in said one side and the other side of said transverse wall to provide a reduced thickness in said transverse wall, and said tubular member being disposed in another one of said sections.

16. A dental retaining splint comprising a bar-like body member having at least one tubular member, said tubular member extending perpendicularly from said body member for being received in a bore provided in a first tooth with said body member being disposable in a channel extending from the first tooth to at least one adjacent tooth, said tubular member including axial opening means extending therethrough for guiding a drill during formation of a pilot hole in the first tooth, said body member including means longitudinally spaced from said tubular member for securing said body member to the adjacent tooth, whereby the pilot hole functions as a lead hole for the formation of said bore in the first tooth, said body member having serpentined front and rear walls to define longitudinally adjacent sections therein, at least one of said sections including a set of aligned dimples to provide a reduced thickness in said body member, and said tubular member being disposed in another one of said sections.

17. A dental retaining splint in combination with a retaining clip receivable therein, said dental retaining splint comprising a bar-like body member having at least one tubular member, said tubular member extending perpendicularly from said body member for being received in a bore provided in a first tooth with said body member being disposable in a channel extending from the first tooth to at least one adjacent tooth, said tubular member including axial opening means extending therethrough for guiding a drill during formation of a pilot hole in the first tooth, said body member including means longitudinally spaced from said tubular member for securing said body member to the adjacent tooth, whereby the pilot hole functions as a lead hole for the formation of said bore in the first tooth, said body member having a second tubular member extending perpendicularly therefrom in the same direction as said first-mentioned tubular member to define said means for securing said body member to the adjacent tooth, said second tubular member also including axial opening means extending therethrough for guiding the drill during formation of a pilot hole in the adjacent tooth; and said retaining clip including two legs connected together by a bight to define a U-shaped configuration, said legs being spaced apart slightly more than distance between said tubular members to provide resiliency between said legs when said legs are inserted into associated ones of said tubular members to hold said splint thereon.

18. A method for reinforcement and retention of mobile dentition, said method comprising:
forming a channel in a first tooth and extending said channel to at least one adjacent second tooth;
temporarily disposing a dental retaining splint, having at least one tubular member, in said channel across said first and second teeth with the tubular member of said splint being disposed on said first tooth and extending outwardly from said channel;
drilling a pilot hole in said first tooth by using an axial opening through said tubular member as a guide for a first drill performing said drilling;
removing said splint from said channel;
enlarging said pilot hole with a second drill to form a bore with said pilot hole functioning as a lead hole for said second drill;
replacing and securing said splint in said channel with said tubular member disposed in said bore in said first tooth and with means securing said splint in said second tooth; and
filling said channel and covering said splint with a dental material.

19. A dental retaining splint in combination with a retaining clip according to claim 17, wherein said legs of said clip are non-parallel in an untensioned condition, and one leg is longer than the other leg of said clip.

20. A method according to claim 18, wherein said means securing said splint in said second tooth is a second tubular member disposed on said splint, said method further including disposing said second tubular member on said second tooth, drilling a second pilot hole in said second tooth through an axial opening in said second tubular member, enlarging said second pilot hole to form a second bore after said splint is removed from said channel, and disposing said second tubular member in said second bore when said splint is replaced in said channel.

21. A method according to claim 20, further including using a U-shaped clip having legs disposable in said tubular member for positioning said splint in said channel.

22. A method according to claim 21, further including cutting said legs of said U-shaped clip to size of said tubular members, and leaving said legs in said tubular members when said splint is secured in said channel.

23. A method according to claim 18, including cutting said splint to a predetermined length before said temporarily disposing of said splint in said channel.

24. A method according to claim 23, including drilling a hole in said splint and in said second tooth to receive a dental anchor defining said means for securing said splint in said second tooth.

25. A method according to claim 24, including self-threading said dental anchor into said hole in said second tooth.

26. A method according to claim 24, including self-threading said dental anchor into said hole in said splint to secure said dental anchor to said splint.

* * * * *